US00PP19298P2

(12) United States Plant Patent
Hofmann

(10) Patent No.: US PP19,298 P2
(45) Date of Patent: Oct. 7, 2008

(54) ***BEGONIA* PLANT NAMED 'INNBELLAB'**

(50) Latin Name: *Begonia×tuberhydbrida*
Varietal Denomination: Innbellab

(75) Inventor: Silvia Hofmann, Mainz (DE)

(73) Assignee: InnovaPlant GmbH & Co. KG, Gensingen (DE)

( * ) Notice: Subject to any disclaimer, the term of this patent is extended or adjusted under 35 U.S.C. 154(b) by 0 days.

(21) Appl. No.: 11/888,425

(22) Filed: Aug. 1, 2007

(51) Int. Cl.
*A01H 5/00* (2006.01)

(52) U.S. Cl. ..... Plt./348
(58) Field of Classification Search ..... Plt./348
See application file for complete search history.

*Primary Examiner*—Kent L Bell
(74) *Attorney, Agent, or Firm*—C. A. Whealy

(57) ABSTRACT

A new and distinct cultivar of *Begonia* plant named 'Innbellab', characterized by its compact, mounded and pendulous plant habit; freely branching habit; and numerous flowers that are pale pink in color.

1 Drawing Sheet

Botanical designation: *Begonia×tuberhybrida.*
Cultivar denomination: 'INNBELLAB'.

BACKGROUND OF THE INVENTION

The present invention relates to a new and distinct cultivar of *Begonia* plant, botanically known as *Begonia× tuberhybrida,* commercially known as hybrid tuberose *Begonia,* and hereinafter referred to by the name 'Innbellab'.

The new *Begonia* is a product of a planned breeding program conducted by the Inventor in Gensingen, Germany. The objective of the breeding program was to develop new hybrid tuberose *Begonia* cultivars with attractive flower form and color.

The new *Begonia* originated from a cross-pollination made by the Inventor in 2003 of the *Begonia×tuberhybrida* cultivar Elserta, not patented, as the female, or seed, parent with an unidentified selection of *Begonia×tuberhybrida,* not patented, as the male, or pollen, parent. The new *Begonia* was discovered and selected by the Inventor from within the progeny of the stated cross-pollination in a controlled environment in Gensingen in 2004.

Asexual reproduction of the new *Begonia* by cuttings in a controlled environment in Gensingen, Germany since 2004, has shown that the unique features of this new *Begonia* are stable and reproduced true to type in successive generations.

SUMMARY OF THE INVENTION

The cultivar Innbellab has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Innbellab'. These characteristics in combination distinguish 'Innbellab' as a new and distinct cultivar of *Begonia:*

1. Compact, mounded and pendulous plant habit.
2. Freely branching habit.
3. Numerous flowers that are pale pink in color.

Plants of the new *Begonia* differ from plants of the female parent, the cultivar Elserta, in the following characteristics:

1. Plants of the new *Begonia* have larger flowers than plants of the cultivar Elserta.
2. Plants of the new *Begonia* and the cultivar Elserta differ in flower color as plants of the cultivar Elserta have orange red-colored flowers.

Plants of the new *Begonia* differ from plants of the male parent selection in the following characteristics:

1. Plants of the new *Begonia* are more freely branching than plants of the male parent selection.
2. Plants of the new *Begonia* have larger flowers than plants of the male parent selection.
3. Plants of the new *Begonia* and the male parent selection differ in flower color as plants of the male parent selection have white-colored flowers.

Plants of the new *Begonia* can be compared to plants of the cultivar Champagner, not patented. In side-by-side comparisons conducted in Gensingen, Germany, plants of the new *Begonia* differed from plants of the cultivar Champagner in the following characteristics:

1. Plants of the new *Begonia* were more freely branching than plants of the cultivar Champagner.
2. Leaves of plants of the new *Begonia* were smaller than leaves of plants of the cultivar Champagner.
3. Plants of the new *Begonia* and the cultivar Champagner differed in flower color as plants of the cultivar Champagner had soft yellow-colored flowers.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph at the bottom of the sheet comprises a side perspective view of a typical flowering plant of 'Innbellab' grown in a container.

The photograph at the top of the sheet is a close-up view of typical flowers and flower buds of 'Innbellab'.

DETAILED BOTANICAL DESCRIPTIONS

In the following description, color references are made to The Royal Horticultural Society Colour Chart, 1995 Edition, except where general terms of ordinary dictionary significance are used. Plants used for the aforementioned photograph and following observations and measurements were grown in Bonsall, Calif. in 20-cm containers and under commercial practice in a polycarbonate-covered greenhouse during the spring and summer. During the production of the plants, day temperatures averaged 21° C., night temperatures averaged 18° C. and light levels were about 5,000 foot-candles. Plants used for the photographs and the description were about four months from planting.

Botanical classification: *Begonia×tuberhybrida* cultivar Innbellab.

Parentage:

*Female, or seed, parent.*—*Begonia×tuberhybrida* cultivar Elserta, not patented.

*Male, or pollen, parent.*—Unidentified selection of *Begonia×tuberhybrida,* not patented.

Propagation:

*Type.*—By terminal vegetative cuttings.

*Time to initiate roots, summer.*—About 15 days at temperatures of about 18° C.

*Time to initiate roots, winter.*—About 25 days at temperatures of about 18° C.

*Time to produce a rooted young plant, summer.*—About 25 days at temperatures of about 18° C.

*Time to produce a rooted young plant, winter.*—About 30 to 35 days at temperatures of about 18° C.

*Root description.*—Medium to thin, fibrous; ivory in color. Plants of the new *Begonia* have not been observed to form tubers.

*Rooting habit.*—Moderately branching; moderately dense.

Plant description:

*Plant form.*—Compact, mounded and pendulous plant habit; freely basal branching with about ten primary branches per plant; primary branches with secondary branches at potentially every node. Moderately vigorous growth habit.

*Plant height.*—About 22 cm.

*Plant width.*—About 48 cm.

*Branch description.*—Length: About 20.5 cm. Diameter: About 9 mm. Internode length: About 2.8 cm. Texture: Smooth, glabrous. Color: 148C tinted with 181D.

*Leaf description.*—Arrangement: Alternate, simple. Length: About 11.5 cm. Width: About 4 cm. Shape: Lanceolate with reniform tendencies. Apex: Acuminate. Base: Obliquely cordate. Margin: Serrate. Texture, upper and lower surfaces: Smooth, glabrous. Venation pattern: Palmate to pinnate. Color: Developing leaves, upper surface: 138A. Developing leaves, lower surface: 147C. Fully expanded leaves, upper surface: 137B; venation, 138A. Fully expanded leaves, lower surface: 147C; venation, 147C. Petiole length: About 3.3 cm. Petiole diameter: About 2.5 mm. Petiole texture, upper and lower surfaces: Smooth, glabrous; occasionally with scattered hairs. Petiole color, upper and lower surfaces: 174D.

Flower description:

*Flowering habit.*—Sterile double flowers with numerous tepals and pistillate single flowers with four to five tepals; flowers axillary and typically arranged in pendulous clusters of two. Freely flowering habit with about eight flowers and flower buds per branch. Flowers not fragrant.

*Natural flowering season.*—Plants flower continuously during the spring in Germany. Flowers last about four to five days on the plant. Flowers not persistent.

*Flowers.*—Shape, double and single flowers: Rounded to ovate. Diameter, double flowers: About 6.8 cm. Diameter, single flowers: About 5.4 cm. Depth (height), double flowers: About 3.5 cm. Depth (height), single flowers: About 3 cm.

*Flower buds.*—Shape, double and single flowers: Ovoid. Length, double flowers: About 2.8 cm. Length, single flowers: About 3.6 cm. Diameter, double flowers: About 2.7 cm. Diameter: single flowers: About 2.1 cm. Color, double and single flowers: Close to 155A tinted with 54D.

*Tepals.*—Arrangement, double and single flowers: Rosette. Quantity per flower, double flowers: About 115 in numerous whorls. Quantity per flower, single flowers: About three to five in a single whorl. Length, double flowers: About 3.2 cm. Length, single flowers: About 2.7 cm. Width, double flowers: About 1.2 cm. Width, single flowers: About 2 cm. Shape, double and single flowers: Elliptical. Apex, double and single flowers: Acute. Base, double and single flowers: Attenuate. Margin, double and single flowers: Entire. Texture, double and single flowers, upper and lower surfaces: Smooth, glabrous. Color, double and single flowers: When opening, upper surface: 155C. When opening, lower surface: 155D. Fully opened, upper surface: 155D tinted with 56B; pink tinting most prominent towards the margins. Fully opened, lower surface: 155D tinted with 56C to 56D; pink tinting most prominent towards the margins.

*Flower bracts.*—Quantity/arrangement: Present on double and single flowers; two, opposite. Length: About 2.6 cm. Shape: Elliptical. Apex: Acute. Base: Truncate. Margin: Entire. Texture, upper and lower surfaces: Smooth, glabrous. Color, upper surface: 155D; towards the margins, tinted with 54D. Color, lower surface: 54D.

*Peduncles.*—Angle: Drooping. Length, double flowers: About 3.8 cm. Length, single flowers: About 2.5 cm. Diameter, double and single flowers: About 2 mm. Texture, double and single flowers: Smooth, glabrous. Color, double and single flowers: Lighter than 182D.

*Reproductive organs.*—Stamens: None observed on double or single flowers. Pistils: Only observed on single flowers. Pistil length: About 2.6 cm. Stigma shape: Irregular, undulate. Stigma color: 17C. Style length: About 6 mm. Style color: 17D. Ovary color: 145B tinted with 182B.

*Seed/fruit.*—Seed and fruit production have not been observed.

Disease/pest resistance: Resistance to pathogens and pests common to *Begonia* has not been observed.

Temperature tolerance: Plants of the new *Begonia* have been observed to tolerate temperatures from about 16° C. to about 35° C.

It is claimed:

1. A new and distinct *Begonia* plant named 'Innbellab' as illustrated and described.

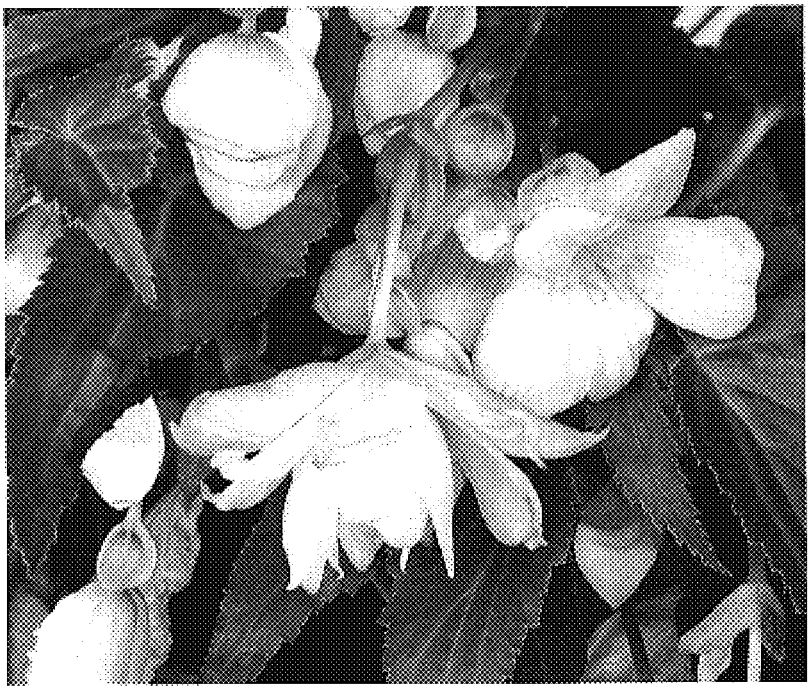
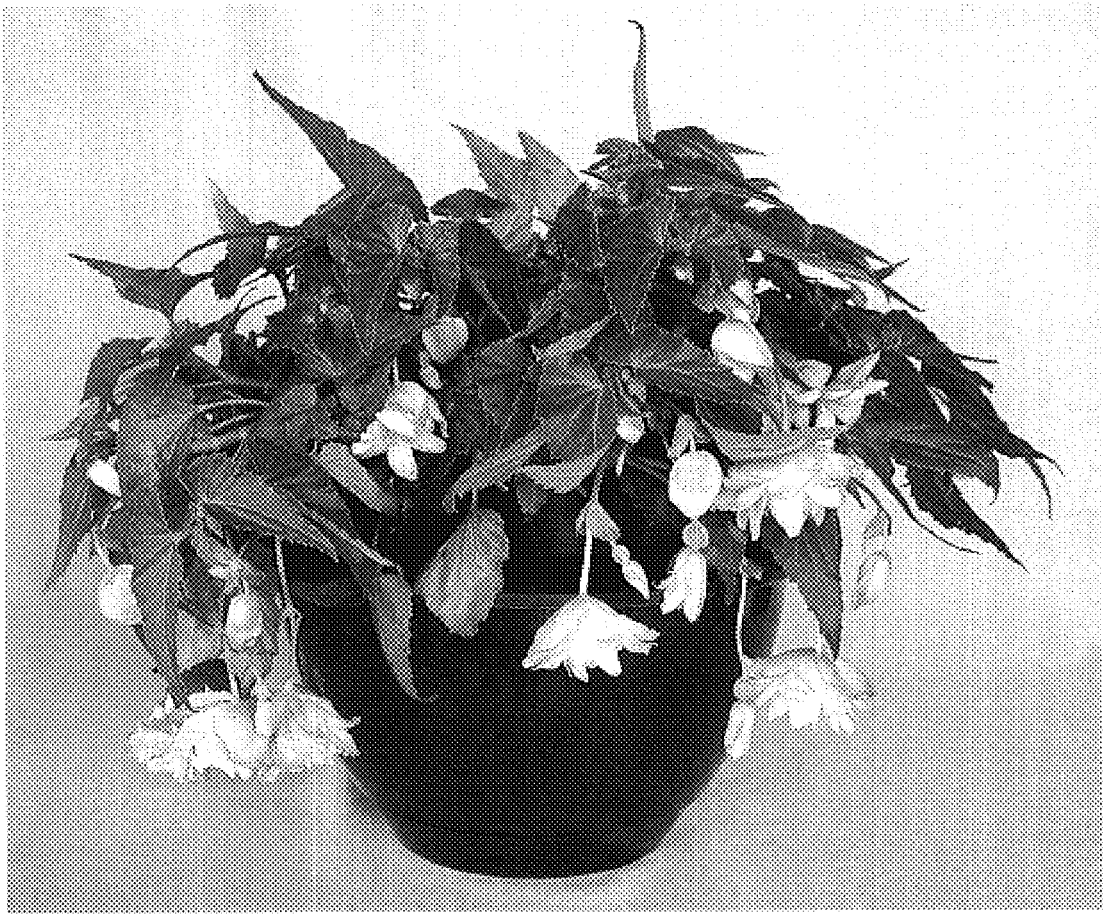

* * * * *